(12) United States Patent
Lartonoix (10) Patent No.: US 8,435,202 B2
(45) Date of Patent: May 7, 2013

(54) HIP, GROIN, AND THIGH SUPPORT DEVICE

(76) Inventor: John P. Lartonoix, St. Louis, MO (US)

( * ) Notice: Subject to any disclaimer, the term of this patent is extended or adjusted under 35 U.S.C. 154(b) by 328 days.

(21) Appl. No.: 12/909,143

(22) Filed: Oct. 21, 2010

(65) Prior Publication Data

US 2011/0092866 A1 Apr. 21, 2011

Related U.S. Application Data (60) Provisional application No. 61/352,558, filed on Jun. 8, 2010, provisional application No. 61/255,906, filed on Oct. 29, 2009.

(51) Int. Cl.
*A61F 13/00* (2006.01)

(52) U.S. Cl.
USPC .................. 602/62; 602/60; 602/61

(58) Field of Classification Search .......... 602/19, 602/23, 24, 60–64; 2/69, 79, 228; 428/124
See application file for complete search history.

(56) References Cited

U.S. PATENT DOCUMENTS

| | | | | |
|---|---|---|---|---|
| 976,564 | A * | 11/1910 | Goodson | 128/845 |
| 4,709,692 | A * | 12/1987 | Kirschenberg et al. | 602/19 |
| 4,977,893 | A * | 12/1990 | Hunt | 602/61 |
| 5,267,928 | A * | 12/1993 | Barile et al. | 482/124 |
| 5,286,251 | A * | 2/1994 | Thompson et al. | 602/23 |
| 5,423,852 | A * | 6/1995 | Daneshvar | 606/201 |
| 5,425,702 | A * | 6/1995 | Carn et al. | 602/62 |
| 5,814,001 | A * | 9/1998 | Schwenn et al. | 602/24 |
| 5,928,175 | A * | 7/1999 | Tanaka | 602/75 |
| 6,652,596 | B2 * | 11/2003 | Smith et al. | 623/32 |
| 7,758,481 | B2 * | 7/2010 | Drennan | 482/124 |
| 8,172,780 | B2 * | 5/2012 | Brown | 602/24 |
| 8,214,926 | B2 * | 7/2012 | Brown | 2/228 |
| 2002/0082537 | A1 * | 6/2002 | MacAllister | 602/4 |
| 2003/0009120 | A1 * | 1/2003 | MacAllister | 602/23 |
| 2004/0116260 | A1 * | 6/2004 | Drennan | 482/124 |
| 2004/0230150 | A1 * | 11/2004 | West | 602/19 |
| 2007/0027419 | A1 * | 2/2007 | Drennan | 602/19 |
| 2010/0292622 | A1 * | 11/2010 | Weissleder et al. | 602/23 |

FOREIGN PATENT DOCUMENTS

CA 2338960 A1 * 12/2001

* cited by examiner

*Primary Examiner* — Kim M Lewis
(74) *Attorney, Agent, or Firm* — Armstrong Teasdale LLP (57) ABSTRACT

A supportive orthotic device is described herein for supporting the hip, groin, and/or thigh of a user. The device has a waist region sized to extend around the waist of the user. The device also has a first surface and a second surface coupled to the waist region. A thigh strap has a first end extending from the first surface of the device and a second end selectively coupled to the second surface and wraps around the user's thigh in a fastened configuration. A groin strap has a first end extending from the first surface of the device and a second end selectively coupled to the second surface and wraps around the user's groin area in a fastened configuration.

20 Claims, 8 Drawing Sheets

HIP, GROIN, AND THIGH SUPPORT DEVICE

CROSS-REFERENCE TO RELATED APPLICATIONS

This applications claims priority to U.S. Provisional Patent Application No. 61/352,558 filed Jun. 8, 2010, and U.S. Provisional Patent Application No. 61/255,906 filed Oct. 29, 2009, the entire disclosures of which are hereby incorporated in their entirety.

BACKGROUND OF THE INVENTION

The field of the invention relates generally to supportive orthotic devices, and more particularly, to athletic supportive devices designed to orthotically support the hip, groin, and/or thigh of a user.

Orthotic devices (i.e., orthoses) are generally worn to support or to correct musculoskeletal deformities and/or abnormalities of the human body. Said devices are typically configured to be in direct contact against a portion of the body of a user. For example, orthotic devices may be designed to be worn directly against any of the extremities of the user or any other portion of the user, such as the user's spine. Rigid or elastic structures may be incorporated into orthotic devices to cause the devices to resist movement in one or more directions. Accordingly, when in use, an orthotic device may restrict or restrain movement in portion of the user's body while supporting either that portion or another portion of the user's body.

Previous orthotic devices have either provided only support and/or restriction to a portion of the user's body, or have provided unsatisfactory results in promoting adduction of the hips or thighs of a user, preventing abduction of the hips or thighs, or supporting the groin or thighs of the user.

DETAILED DESCRIPTION OF THE INVENTION

Figure 1:
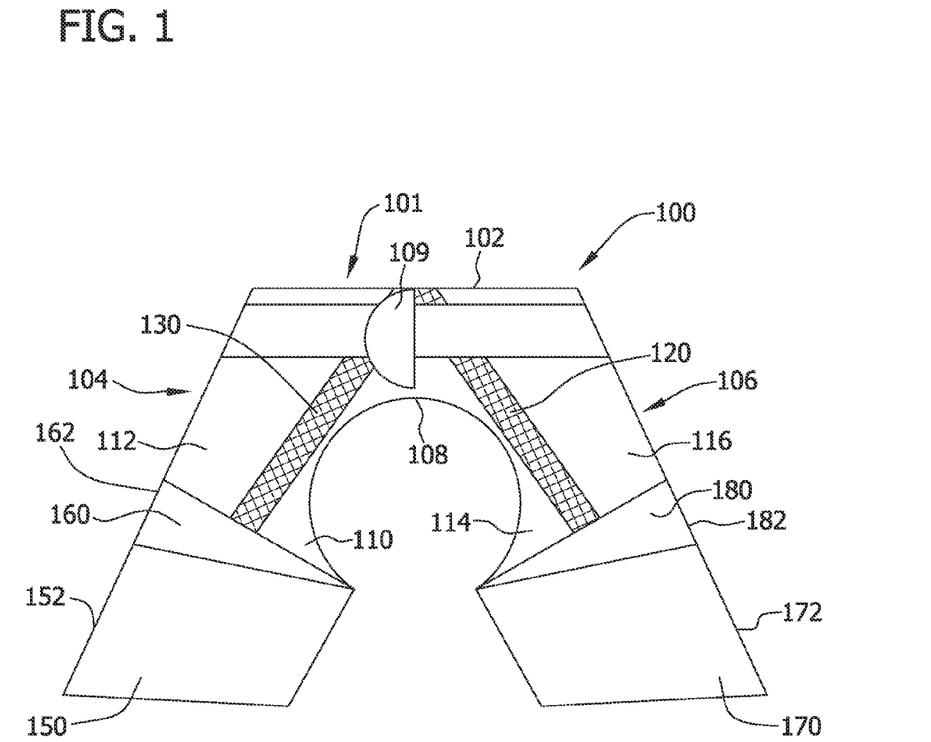
FIG. 1 is a front view of an exemplary orthotic device in a fastened configuration.

The embodiments described herein are directed to a supportive orthotic device, shown generally at 100 in FIGS. 1-6. FIG. 1 is a front (i.e., anterior) view of an exemplary supportive orthotic device 100 (referred to hereinafter as "the device" and described in more detail below) for use in supporting the hips, thighs, and/or groins of a user 201. The device is generally worn about the user's 201 midsection, as shown in FIGS. 4-8, and promotes adduction of the hips 203 and thighs 205 of the user while resisting abduction of the hips and thighs.

Figure 2:
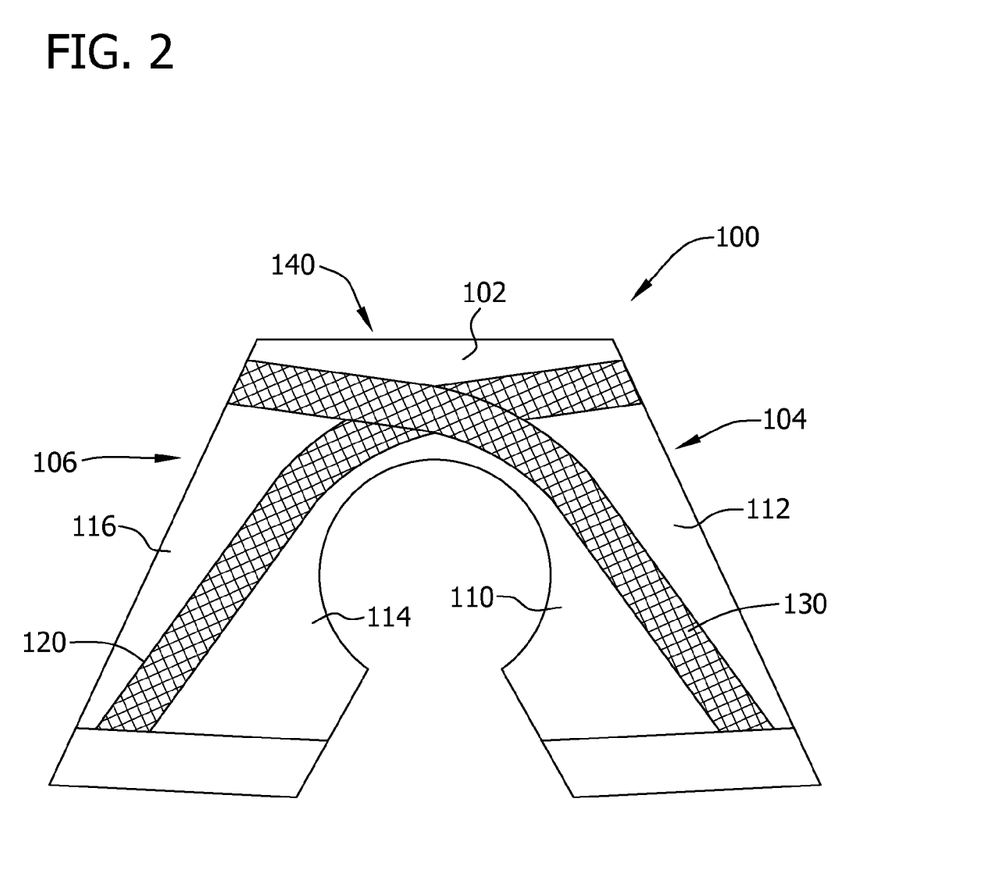
FIG. 2 is a rear view of the orthotic device shown in FIG. 1.
Figure 3:
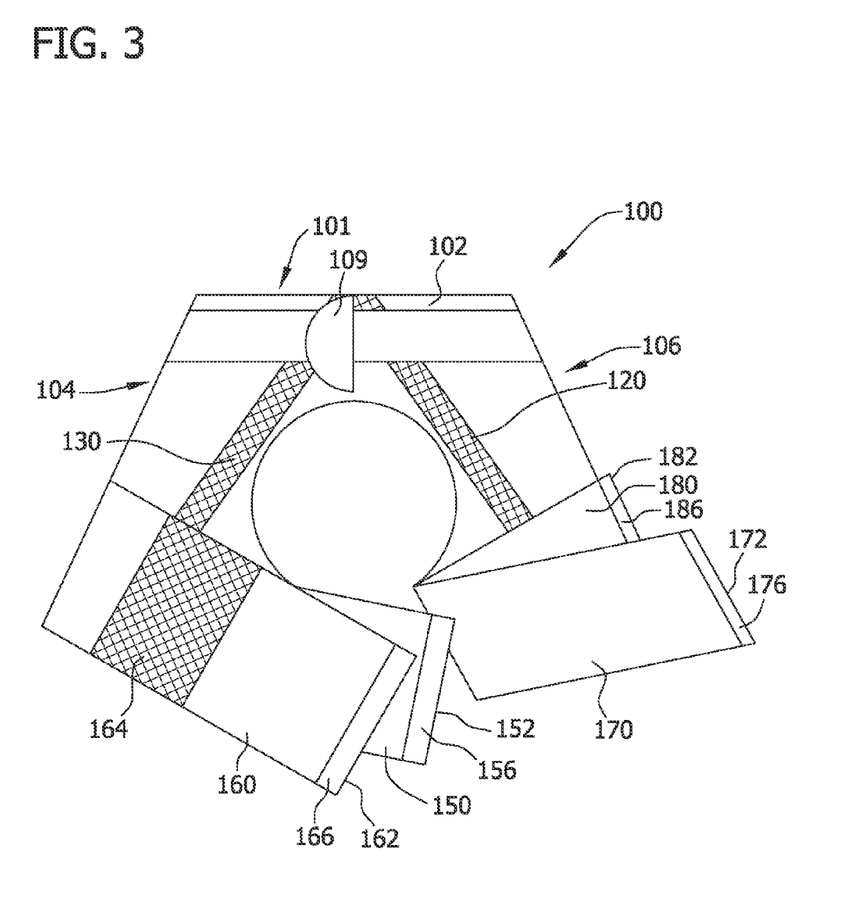
FIG. 3 is a front view of the orthotic device shown in FIG. 1 in an unfastened configuration.

A front surface 101 of device 100 is illustrated in FIGS. 1 and 3 and an opposite rear surface 140 is illustrated in FIG. 2. Device 100 is designed to be worn by the human user 201 (depicted in phantom in FIGS. 4-7) and is constructed from a variety of suitable materials, such as, but not limited to, neoprene, cotton, synthetic cotton blends, synthetic materials, or any other suitable fabric-like compliant material.

In the exemplary embodiment, device 100 has a waist region 102, a right thigh region 104, a left thigh region 106, and a crotch region 108. Right thigh region 104 has an inner portion 110 and an outer portion 112. Similarly, left thigh region 106 has an inner portion 114 and an outer portion 116. When worn by user 201, inner portions 110, 114 are closer to a mid-sagittal plane S (FIG. 4) of the user than outer portions 112, 116. The mid-sagittal plane S of the user 201 is an imaginary plane that substantially from the top of the user near its head to the bottom of the user near its feet along the Y axis and divides the body of the user into two halves of equal portions.

Figure 4:
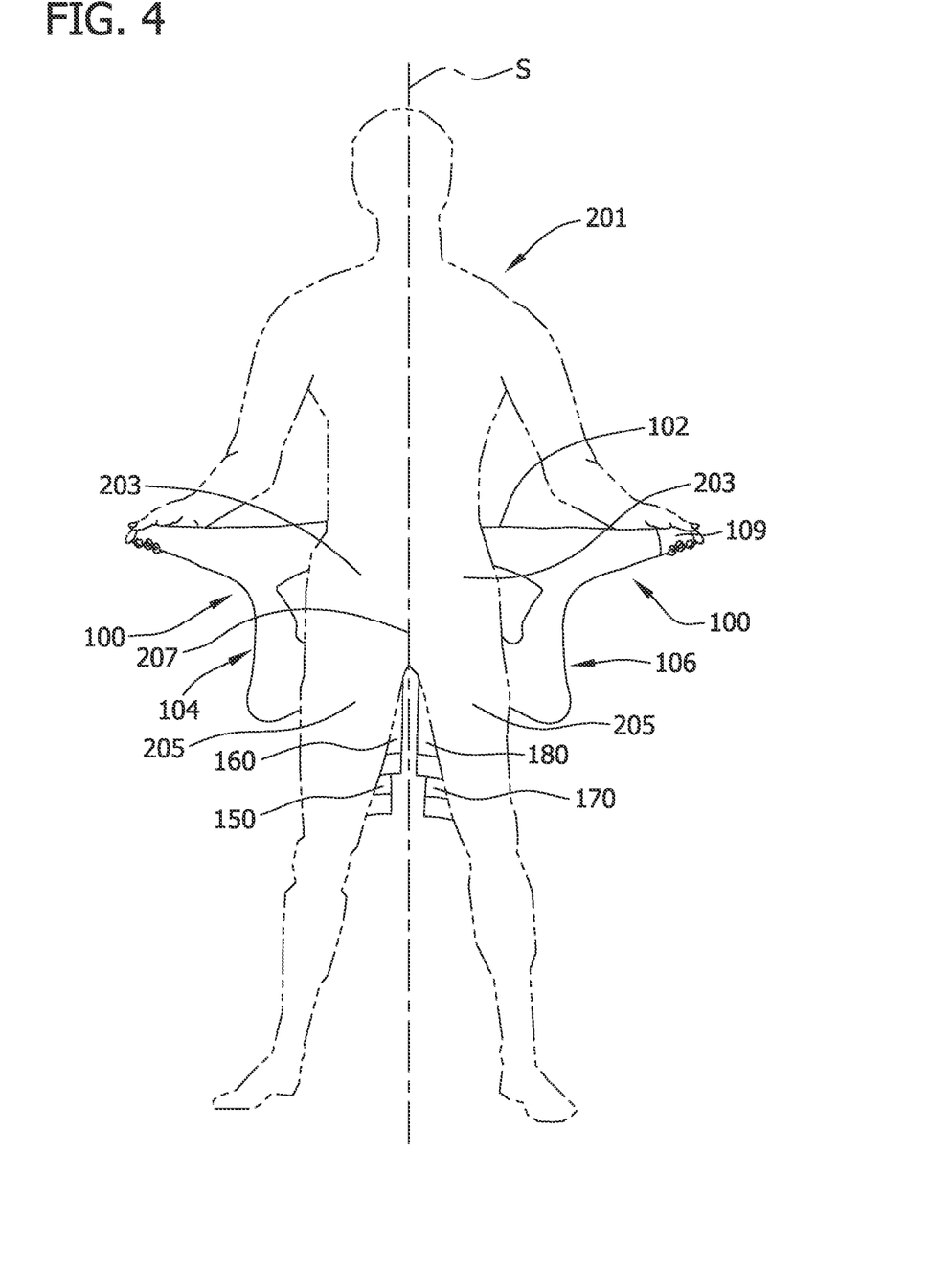
FIG. 4 is a front view of a user initially donning the orthotic device shown in FIG. 1 without any of the fastening straps fastened.

In the exemplary embodiment, waist region 102 is independently separable from a fastened position (illustrated in FIG. 1) to an unfastened position (illustrated in FIG. 4). Waist region 102 is securable in the fastened position via a closure 109. Closure 109 may be a hook and loop type fastener, a zipper, a button, a snap, and/or any other suitable releasable fastening and/or coupling mechanism that enables waist region 102 to function as described herein. In other embodiments, waist region 102 is not selectively separable from a fastened positioned to an unfastened position. Rather, in such an embodiment, waist region 102 is permanently configured in the fastened configuration and the 201 user dons device 100 by inserting both of their legs through waist region 102.

A left abduction strap 120 extends from left thigh region 106. Left abduction strap 120 extends generally along the full length of left thigh region 106 from waist region 102. Left abduction strap 120 may be coupled to left thigh region 106 via any suitable mechanism, such as, but not limited to, sewing or adhesive. In the exemplary embodiment, left abduction strap 120 is a strip of elastic-like material that has a ratio of percent elongation per force applied thereto that is less than that of the material used in fabricating left thigh region 106. As such, left abduction strap 120 facilitates increasing the amount of force necessary to elongate left thigh region 106. Left abduction strap 120 may be fabricated from any suitable material, such as neoprene or any other resilient material that enables left abduction strap to function as described above. In some embodiments, both left thigh region 106 and left abduction strap 120 are fabricated from the same type of material (i.e., neoprene) having different mechanical properties. For example, left abduction strap 120 may be fabricated from a neoprene-like material that has a ratio of percent elongation per force applied thereto that is less than a neoprene-like material from which left thigh region 106 is fabricated. In other embodiments, left abduction strap 120 may be formed integrally with the left thigh region 106. In such embodiments, the composition of left thigh region 106 is altered to enable left abduction strap 120 to formed with the mechanical properties described above. For example, the composition of left thigh region 106 may be altered to form the left abduction strap 120 with material that has an increased density (e.g., by increasing the thread or fiber count per unit area) in the portion of the left thigh region corresponding to the left abduction strap.

The right abduction strap 130 is similar in configuration to the left abduction strap 120. Right abduction strap 130 extends from right thigh region 104. Right abduction strap 130 extends generally along the full length of right thigh region 104 from waist region 102. Right abduction strap 130 may be coupled to right thigh region 104 via any suitable mechanism, such as, but not limited to, sewing or adhesive. In the exemplary embodiment, right abduction strap 130 is a strip of elastic-like material that has a ratio of percent elongation per force applied thereto that is less than that of the material used in fabricating right thigh region 104. As such, right abduction strap 130 facilitates increasing the amount of force necessary to elongate right thigh region 104. Right abduction strap 130 may be fabricated from any suitable material, such as neoprene or any other resilient material that enables right abduction strap to function as described above. In some embodiments, both right thigh region 104 and right abduction strap 130 are fabricated from the same type of material (i.e., neoprene) having different mechanical properties. For example, right abduction strap 130 may be fabricated from a neoprene-like material that has a ratio of percent elongation per force applied thereto that is less than a neoprene-like material from which right thigh region 104 is fabricated. In other embodiments, right abduction strap 130 may be formed integrally with the right thigh region 104. In such embodiments, the composition of right thigh region 104 is altered to enable right abduction strap 130 to formed with the mechanical properties described above. For example, the composition of right thigh region 104 may be altered to form the right abduction strap 130 with material that has an increased density (e.g., by increasing the thread or fiber count per unit area) in the portion of the right thigh region corresponding to the right abduction strap.

As best seen in FIG. 2, left abduction strap 120 and right abduction strap 130 extend from rear surface 140. Alternatively, left abduction strap 120 and right abduction strap 130 do not extend from rear surface 140. Moreover, in still other embodiments, abduction straps 120 and 130 are not used with device 100.

A right thigh strap 150 and a right groin strap 160 (collectively "straps 150, 160") are shown in a fastened configuration in FIG. 1 and in an unfastened configuration in FIG. 3. The straps 150, 160 are not shown in FIG. 2 for the sake of clarity. Straps 150, 160 extend from and are coupled at respective first ends to the rear surface 140 of device 100 by a permanent coupling mechanism (e.g., sewing or adhesive). At respective second ends 152, 162 the straps 150, 160 are selectively coupled to the front surface 101 of device 100 in the right thigh region 104 by a coupling mechanism. In the exemplary embodiment, the coupling mechanism includes portions 156, 166 that are selectively coupled to right thigh region 104. Alternatively, straps 150, 160 extend from and are coupled at respective first ends to the front surface 101 of device 100 by a permanent coupling mechanism (e.g., sewing or adhesive) and respective second ends 152, 162 of straps 150, 160 are selectively coupled to the rear surface 140 of device 100 by a coupling mechanism.

Straps 150, 160 are fabricated from an elastic material (e.g., neoprene). In one embodiment, either or both of the straps 150, 160 are fabricated with a material having a portion with different mechanical properties than the rest of the strap. In the embodiment of FIG. 3, right thigh region 104 is formed with a section 164 that is permanently affixed to front surface 101 and rear surface 140, thus forming a closed right thigh section. Section 164 generally functions to assist the user 201 in donning device 100 by ensuring that user 201 places their leg through the opening enclosed by the front surface 101, rear surface 140, and section 164. While not illustrated, left thigh region 106 may also be fabricated with a section that is substantially similar to or is fabricated the same as section 164. In some embodiments, device 100 does not include section 164.

During use, straps 150, 160 are fastened to device 100 by wrapping the straps from the rear surface 140 inward towards to mid-sagittal plane S. Straps 150, 160 are then passed over inner portion 110 and towards outer portion 112 of front surface 101. Straps 150, 160 are then coupled at respective second ends 152, 162 to right thigh region 104. In some embodiments, right thigh strap 150 is permanently secured (e.g., by sewing or adhesive) to right thigh region 104 to form a thigh cuff A left thigh strap 170 and a left groin strap 180 (collectively "straps 170, 180") are shown in a fastened configuration in FIG. 1 and in an unfastened configuration in FIG. 3. The straps 170, 180 are not shown in FIG. 2 for the sake of clarity. Straps 170, 180 extend from and are coupled at respective first ends to the rear surface 140 of device 100 by a permanent coupling mechanism (e.g., sewing or adhesive). At respective second ends 172, 182 the straps 170, 180 are selectively coupled to the front surface 101 of device 100 in the left thigh region 106 by a coupling mechanism. In the exemplary embodiment, the coupling mechanism includes portions 176, 186 that are selectively coupled to left thigh region 106. Alternatively, strap 170, 180 extend from and are coupled at respective first ends to front surface 101 of device 100 by a permanent coupling mechanism (e.g., sewing or adhesive) and respective second end 172, 182 of straps 170, 180 are selectively coupled to the rear surface 140 of device 100 by a coupling mechanism.

Straps 170, 180 are fabricated from an elastic material (e.g., neoprene). In one embodiment, either or both of the straps 170, 180 are fabricated with a material having a portion with different mechanical properties than the rest of the strap. In the embodiment of FIG. 3, left thigh region 106 is formed with a section 164 that is permanently affixed to front surface 101 and rear surface 140, thus forming a closed left thigh section. Section 164 generally functions to assist the user 201 in donning device 100 by ensuring that user 201 places their leg through the opening enclosed by the front surface 101, rear surface 140, and section 164. While not illustrated, left thigh region 106 may also be fabricated with a section that is substantially similar to or is fabricated the same as section 164. In some embodiments, device 100 does not include section 164. The straps 170, 180 are applied in a manner similar to, or the same as, straps 150, 160.

FIGS. 4-8 depict various steps that user 201 may take in donning the device 100. The steps depicted in FIGS. 4-8 are merely exemplary, and do not represent the only order that user 201 may fasten the various straps of device 201. For example, in other embodiments, user 201 may fasten the straps in a different order without departing from the scope of the embodiments.

Figure 5:
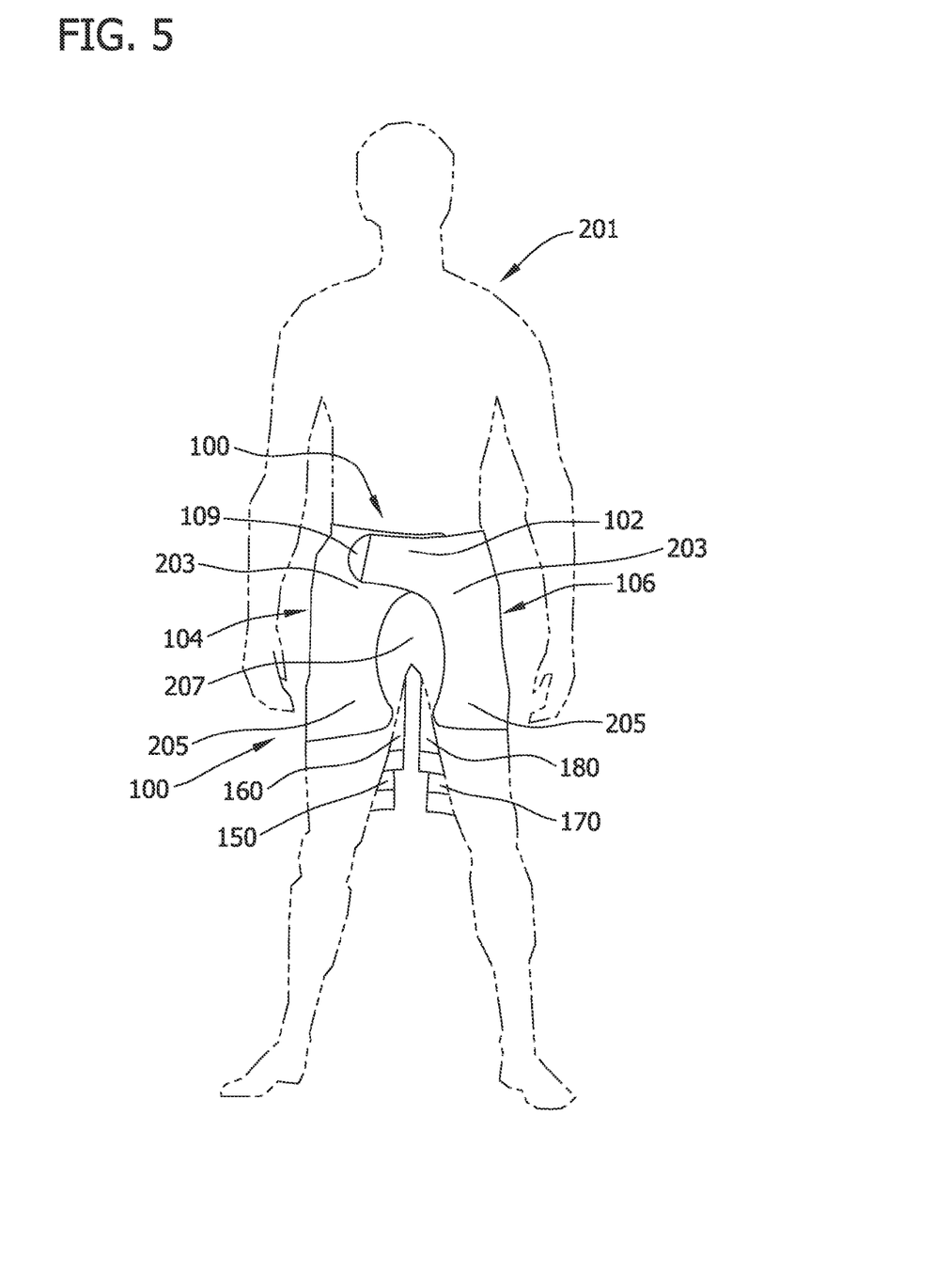
FIG. 5 is a front view of the user after only fastening the waist strap of the orthotic device shown in FIG. 1.
Figure 6:
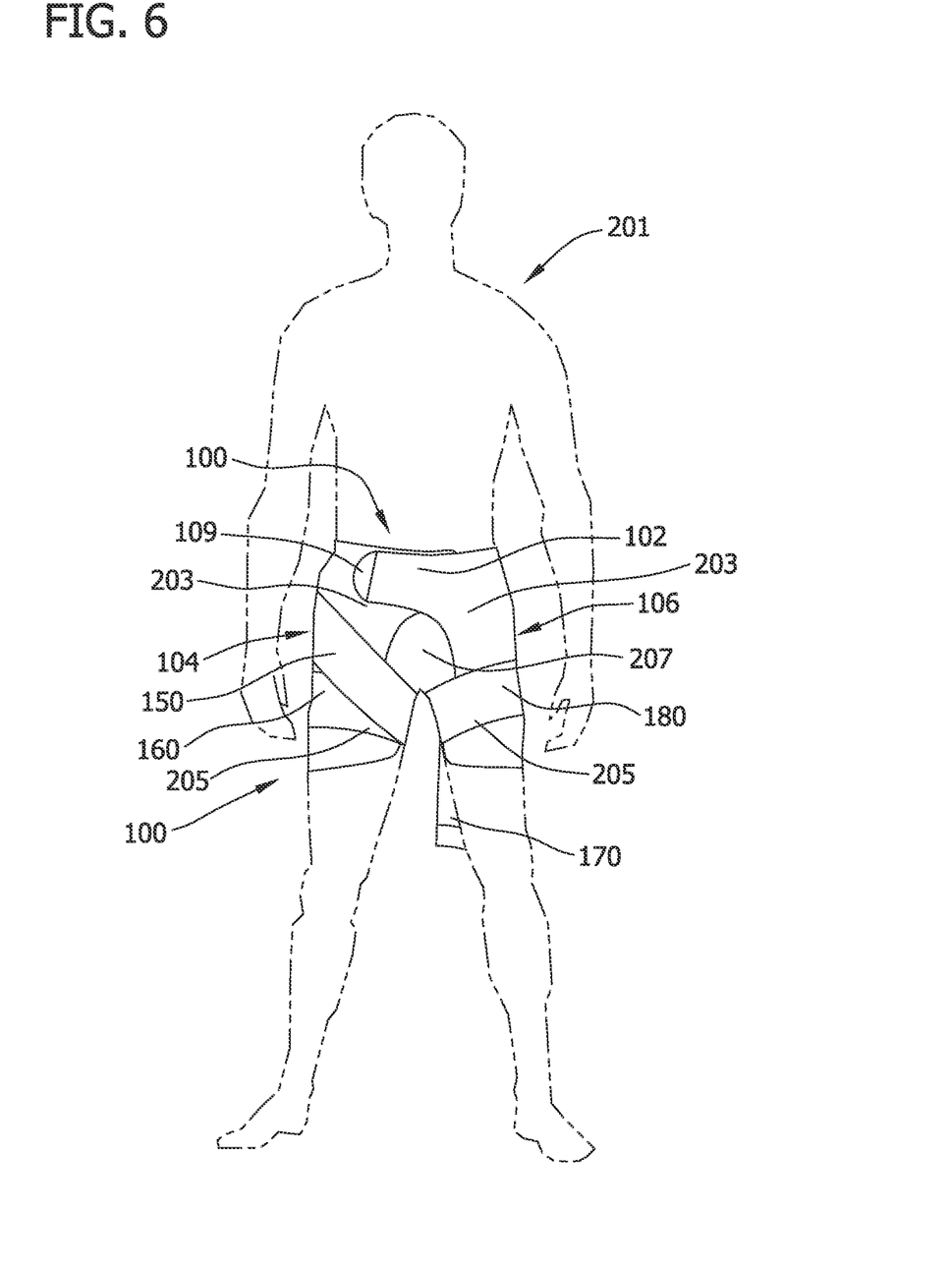
FIG. 6 is a front view of the user after fastening the waist strap and a right groin strap and a right thigh strap and a left groin strappair of support straps and one groin strap of the orthotic device shown in FIG. 1.
Figure 7:
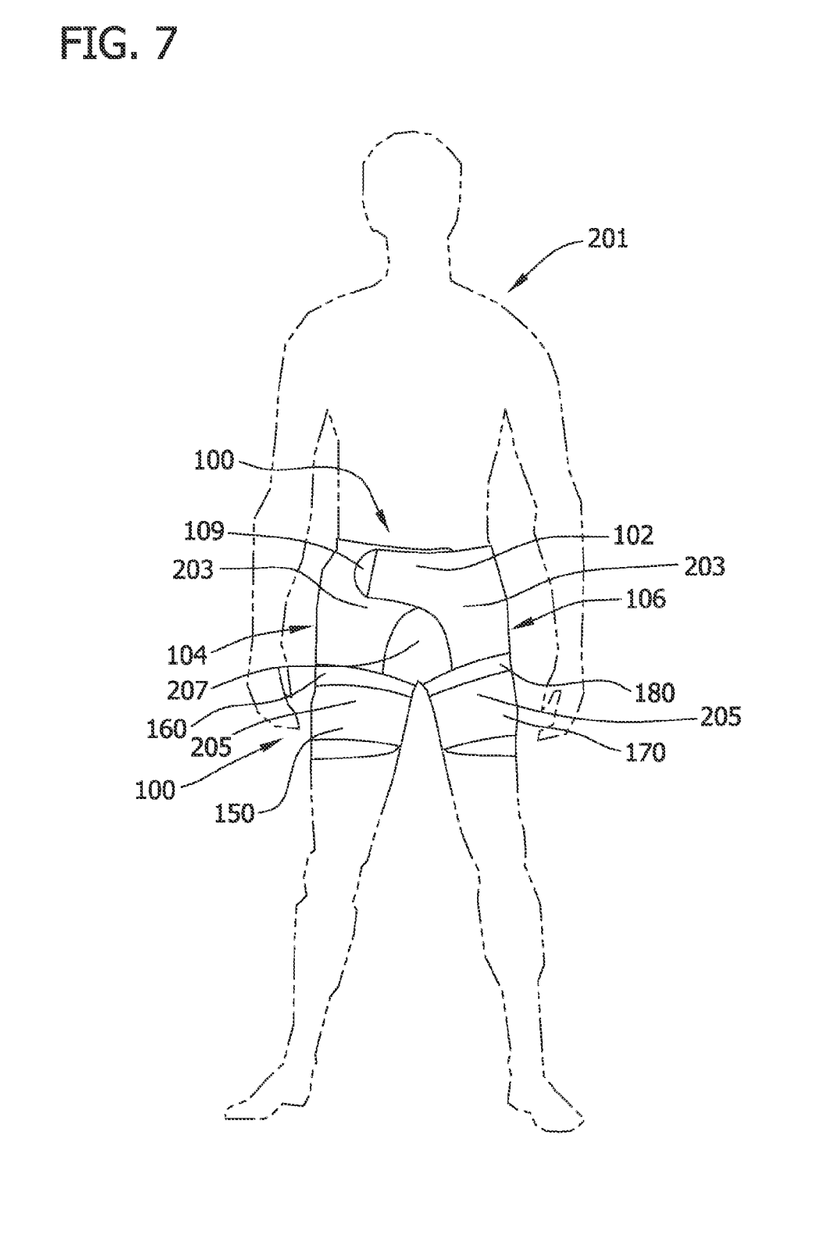
FIG. 7 is a front view of the user after the orthotic device shown in FIG. 1 is completely fastened.
Figure 8:
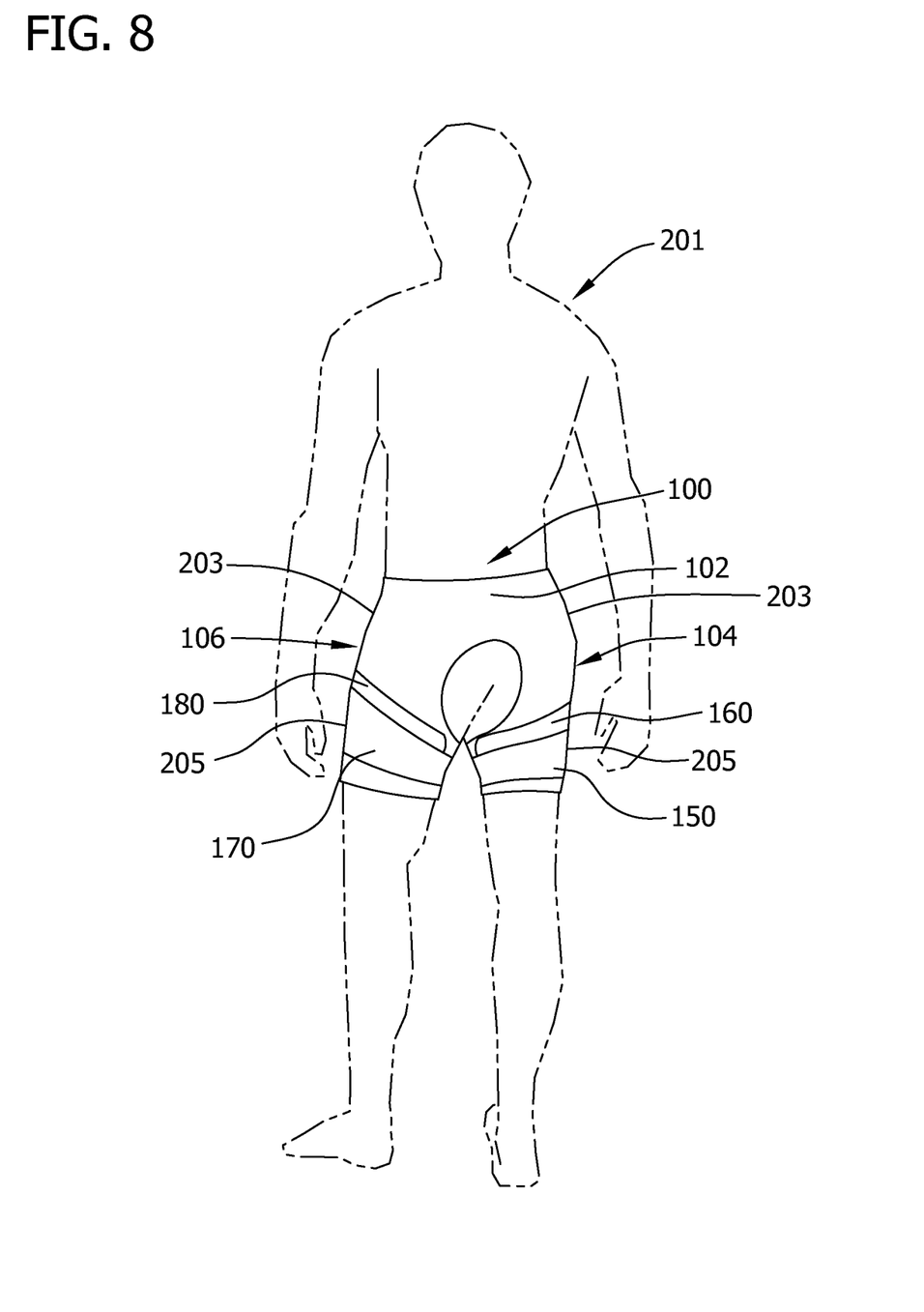
FIG. 8 is a rear view of the user shown in FIG. 7.

The embodiments depicted in FIGS. 4-8 do not include the section 164. Accordingly, as shown in FIG. 4, user 201 initially wraps waist region 102 around their waist. User 201 then fastens the two spaced-apart ends of waist region 102 together to secure the device 100 around their waist, as shown in FIG. 5. The user 201 may then fasten straps 160, 180 as described above. When straps 160, 180 and strap 150 are fastened and strap 170 is unfastened, device 100 appears as shown in FIG. 6. The user 201 then fastens the strap 170 as described above, resulting in the arrangement of the device 100 as shown in FIG. 7. Alternatively, straps 160, 180 may be coupled first to induce appropriate groin support and straps 150, 170 may be coupled subsequently to overlap straps 160, 180 to provide appropriate thigh support. Alternatively, straps 150, 160, 170, and 180 may be fastened in any other order without departing from the scope of the embodiments. FIG. 7 thus shows the user 201 wearing device 100 completely fastened and ready for use. FIG. 8 depicts a rear view of the user 201 with device 100 completely fastened.

When in use, straps 150, 160, 170, 180 promote adduction of the hips 203 and thighs 205 of the user 201 wearing device 100 by inducing circumferential pressure to aid in reducing muscular and ligamentous elongation. The reduction of muscular and ligamentous elongation facilitates reducing the risk of groin and thigh strains. Moreover, abduction straps 120, 130 generally function to facilitate reducing hip abduction, and to promote hip adduction. In turn, movement that would displace the hips 203 and/or thighs 205 of user 201 away from the mid-sagittal plane S of the user's body. Movement that displaces the hips 203 and/or thighs 205 of user 201 away from the mid-sagittal plane S may increase the susceptibly of user 201 to strains, possibly tears, and further injury.

Straps 150, 160, 170, 180 and abduction straps 120, 130 facilitate increasing the stability and biomechanical function of the hips 203, groin 207, and thighs 205 of user 201 wearing device 100. Device 100 aids in the performance of user 201 wearing the device while engaging in athletic events or during other types of strenuous activity. Device 100 facilitates reducing strain to the groin 207 and thighs 205 of user 201 and thus enables the user to increase their athletic performance while at the same time reducing the risk of injury to the user. Device 100 may be worn by user 201 to reduce or prevent injury, or it may be worn by the user after occurrence of an injury to prevent further injury.

In at least one embodiment, device 100 is configured to be worn by user 201 and includes the waist region 102 and right thigh region 104 and left thigh region 106. Right groin strap 160 and right thigh strap 150 are selectively coupled to right thigh region 104 of device 100. Right groin strap 160 is configured to be wrapped around at least a portion of groin 207 and/or hip 203 of user 201. Right thigh strap 160 is configured to be wrapped around at least a portion of thigh 205 of user 201. Left groin strap 180 and left thigh strap 170 are selectively coupled to left thigh region 106 of device 100. Left groin strap 180 is configured to be wrapped around at least a portion of groin 207 and/or hip 203 of user 201. Left thigh strap 170 is configured to be wrapped around at least a portion of thigh 205 of user 201. Right thigh region 104 may have right abduction strap 130 formed therein or otherwise affixed thereto. Left thigh region 106 may have left abduction strap 120 formed therein or otherwise affixed thereto.

In at least one embodiment, device 100 is configured such only one set of straps are used in conjunction with the waist region 102 and closure 109. As such, device 100 is used to support only one side (either the right or left) of the user. For example, in one embodiment device 100 has only the right groin strap 160 and/or right thigh strap 150. The right abduction strap 130 may also be used in the device 100 in this embodiment. Moreover, in another embodiment device 100 has only left groin strap 180 and/or left thigh strap 170. The left abduction strap 120 may be used in the device 100 in this embodiment.

According to still other embodiments, device 100 may use only one strap on one side (e.g., the right side) of the device 100 (e.g., only right thigh strap 150) while two or more straps may be used on the other side (e.g., the left side may use the left thigh strap 170 and the left abduction strap 120). As such, any number of straps described may be used in the device 100 and the other straps not used in the device 100 may be omitted from the device 100 without departing from the scope of the embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A supportive orthotic device for supporting at least one of a hip, a thigh, and a groin of a user, said device comprising:
   a waist region sized to extend around a waist of the user, said device having a front surface and a rear surface coupled to the waist region;
   a thigh strap comprising a first end extending from the rear surface of said device and a second end selectively coupled to the front surface of said device when said device is in a fastened configuration, said thigh strap configured to wrap around the user's thigh when in the fastened configuration;
   a groin strap comprising a first end extending from the rear surface of said device and a second end selectively coupled to the front surface of said device when said device is in a fastened configuration, said groin strap configured to wrap around the user's groin when in the fastened configuration; and
   an abduction strap extending along a thigh region on at least one the front surface and the rear surface of said device.

2. A device in accordance with claim 1, wherein at least one of said thigh strap and said groin strap are fabricated from an elastic material.

3. A device in accordance with claim 1, wherein said waist region has a first portion and a second portion, said first portion and second portion releasably couplable by a waist coupling mechanism.

4. A device in accordance with claim 1, further comprising a coupling mechanism disposed at the second end of said thigh strap for selectively coupling the second end to the front surface of said device when said device is in the fastened configuration.

5. A device in accordance with claim 1, further comprising a coupling mechanism disposed at the second end of said groin strap for selectively coupling the second end to the front surface of said device when said device is in the fastened configuration.

6. A device in accordance with claim 1, wherein said thigh strap is a left thigh strap and is configured to wrap around the user's left thigh when said device is in the fastened configuration and wherein said device further includes a right thigh strap for supporting the user's right thigh, said right thigh strap having a first end extending from the rear surface of said device and a second end selectively coupled to the front surface of said device when said device is in a fastened configuration, said right thigh strap configured to wrap around the user's right thigh when in the fastened configuration.

7. A device in accordance with claim 1, wherein said groin strap is a left groin strap and is wrapped around the user's left groin area when said device is in the fastened configuration and wherein said device further includes a right groin strap for supporting the users right groin area, said right groin strap having a first end extending from the rear surface of said device and a second end selectively coupled to the front surface of said device when said device is in a fastened configuration, said right groin strap configured to wrap around the user's right groin when in the fastened configuration.

8. A device in accordance with claim 1, wherein said abduction strap is fabricated from an elastic material having a rate of percent elongation per force applied thereto that is less than that of a material used to form the thigh region of said device.

9. A supportive orthotic device for supporting at least one of a hip and a thigh of a user, said device comprising:
   a waist region sized to extend around a waist of the user, said device having a front surface and a rear surface;
   a thigh strap comprising a first end extending from the rear surface and a second end selectively coupled to the front surface of said device when said device is in a fastened configuration, said thigh strap configured to wrap around the user's thigh when in the fastened configuration;
   a coupling mechanism disposed on the second end of said thigh strap for selectively coupling the second end of said thigh strap to the front surface of said device; and
   an abduction strap extending along a thigh region on at least one the front surface and the rear surface.

10. A device in accordance with claim 9, wherein said thigh strap is formed from an elastic material.

11. A device in accordance with claim 9, wherein said coupling mechanism includes one component of a hook and loop fastener system.

12. A device in accordance with claim 9, wherein said waist region has a first portion and a second portion, said first portion and second portion releasably couplable by a waist coupling mechanism.

13. A device in accordance with claim 9, further comprising a groin strap having a first end extending from the rear surface of said device and a second end selectively coupled to the front surface of said device when said device is in a fastened configuration, said groin strap configured to wrap around the user's groin when in the fastened configuration.

14. A device in accordance with claim 13, further comprising a coupling mechanism disposed on the second end of said groin strap for selectively coupling the second end of said groin strap to the front surface of said device.

15. A device in accordance with claim 9, wherein said abduction strap is fabricated from an elastic material having a rate of percent elongation per force applied thereto that is less than that of a material used to form the thigh region of said device.

16. A supportive orthotic device for supporting at least one of a hip and a groin of a user, said device comprising:
   a waist region positionable around the waist of the user, said device having a first surface and an opposing second surface coupled to the waist region;
   a groin strap having a first end extending from the first surface of said device and a second end selectively coupled to the second surface of said device when said device is in a fastened configuration, said groin strap configured to wrap around the user's groin when in the fastened configuration;
   a coupling mechanism disposed on the second end of said groin strap for selectively coupling the second end of said thigh strap to the second surface of said device; and
   an abduction strap extending along a thigh region on at least one the first surface and the second surface.

17. A device in accordance with claim 16, wherein the first surface of said device is a rear surface of said device and the second surface of said device is a front surface of said device.

18. A device in accordance with claim 16, wherein the first surface of said device is a front surface of said device and the second surface of said device is a rear surface of said device 19. A device in accordance with claim 18, further comprising a thigh strap having a first end extending from the front surface of said device and a second end selectively coupled to the rear surface of said device when said device is in a fastened configuration, said thigh strap configured to wrap around the user's thigh when in the fastened configuration.

20. A device in accordance with claim 19, further comprising a coupling mechanism disposed on the second end of said thigh strap for selectively coupling the second end of said thigh strap to the rear surface of said device.

* * * * *